(12) United States Patent
Ruvio et al.

(10) Patent No.: US 12,070,266 B2
(45) Date of Patent: Aug. 27, 2024

(54) MICROWAVE ABLATION PROBE WITH CHOKE

(71) Applicant: Varian Medical Systems, Inc., Palo Alto, CA (US)

(72) Inventors: Giuseppe Ruvio, Dublin (IE); Jimmy Edward Eaton-Evans, Galway (IE); Simon Hogan, Galway (IE)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 384 days.

(21) Appl. No.: 17/362,643

(22) Filed: Jun. 29, 2021

(65) Prior Publication Data

US 2022/0409274 A1 Dec. 29, 2022

(51) Int. Cl.
*A61B 18/18* (2006.01)
*A61B 18/00* (2006.01)

(52) U.S. Cl.
CPC . *A61B 18/1815* (2013.01); *A61B 2018/00011* (2013.01); *A61B 2018/00577* (2013.01); *A61B 2018/183* (2013.01)

(58) Field of Classification Search
CPC ........... A61B 18/18; A61B 18/1815; A61B 2018/1823; A61B 2018/183; A61B 2018/1838; A61B 2018/1846; A61B 2018/1853; A61B 2018/1861; A61B 2018/1869; A61B 2018/1892; A61B 2018/00011; A61B 2018/00577; A61B 2018/00023

USPC .......... 606/33; 607/101, 115, 116, 154, 155, 607/156
See application file for complete search history.

(56) References Cited

U.S. PATENT DOCUMENTS

| | | |
|---|---|---|
| 5,376,094 A | 12/1994 | Kline |
| 5,876,398 A | 3/1999 | Mulier et al. |
| 9,861,439 B2 | 1/2018 | Brannan et al. |
| 2011/0077635 A1 | 3/2011 | Bonn |
| 2016/0030112 A1 | 2/2016 | Brannan et al. |
| 2018/0036069 A1* | 2/2018 | Dickhans ........... A61B 18/1492 |
| 2020/0188021 A1* | 6/2020 | Wong ................. A61B 18/1815 |
| 2020/0205894 A1 | 7/2020 | Eaton-Evans et al. |
| 2021/0038303 A1 | 2/2021 | Moseov et al. |
| 2021/0220048 A1* | 7/2021 | Zhang ................ A61B 18/1815 |

FOREIGN PATENT DOCUMENTS

| | | |
|---|---|---|
| AU | 2017202181 B2 | 10/2018 |
| EP | 3025662 B1 | 11/2018 |

(Continued)

OTHER PUBLICATIONS

Partial International Search Report and Written Opinion for PCT/US2022/073002 issued Sep. 27, 2022.

(Continued)

*Primary Examiner* — Thomas A Giuliani
(74) *Attorney, Agent, or Firm* — Duane Morris LLP (57) ABSTRACT

A microwave ablation probe includes a cable comprising an antenna configured to deliver Radio Frequency (RF) energy to a target zone and a cooling path defined by a first channel and a second channel configured to circulate cooling fluid in the probe. The inner tube also comprises a choke formed thereon configured to reduce RF energy reflected away from the antenna.

20 Claims, 10 Drawing Sheets

(56) References Cited

FOREIGN PATENT DOCUMENTS

| WO | 2018192325 A1 | 10/2018 |
| WO | 2023278944 A1 | 1/2023 |

OTHER PUBLICATIONS

Hojatollah, et al., "Antenna Designs for Microwave Tissue Ablation", Crit Rev Biomed Eng., 2018; 46(6): 495-521.
International Search Report and Written Opinion for PCT/US2022/073002 issued Dec. 13, 2022, 19 pages.

\* cited by examiner

MICROWAVE ABLATION PROBE WITH CHOKE

TECHNICAL FIELD

The disclosure relates to microwave ablation probes. More specifically, the disclosure relates to microwave ablation probes that include microwave ablation antennas and a choke.

BACKGROUND

Microwave ablation probes can be used in clinical treatments such as thermal ablation treatments. In such treatments, thermal ablation can be used to destroy undesirable tissue such as malignant cells in a body. A microwave ablation antenna can be included in the probe and be used to deliver Radio Frequency (RF) energy such as microwave energy to a target tissue to heat the target tissue and destroy the target tissue. The microwave ablation antenna can be positioned inside the ablation probe that can position the microwave ablation antenna proximate the target tissue.

In some treatments, the ablation probe is guided to the target tissue though other tissue or near to tissue or body structures that it is desirable not to damage during treatment. It is desirable, therefore, to maintain a small size of the microwave ablation antenna and/or the ablation probe. In this manner, the damage to tissue and other body structures that may be located close to the target tissue to be destroyed is minimized or prevented. It is also desirable that the microwave ablation antenna produce a repeatable and known heating zone relative to the position of the microwave ablation antenna. The heating zone can then be reliably delivered to the target tissue without damaging or with minimized damage to surrounding tissue and body structures. There exists a need, therefore, for improved microwave ablation probes and/or antennas that have a sufficiently small size to prevent undesirable damage that can also reliably and repeatably produce known heating zones.

SUMMARY

The methods and apparatuses described herein are directed to embodiments and example ablation probes that can include a cooling system and a choke to produce an ablation zone having a desired size and shape. In some examples, the ablation probes of the present disclosure can include a choke integrally formed in an inner tube of the probe. The choke can be formed of one or more crimps in which at least a portion of the inner tube is deformed inwardly toward a cable positioned at a center of the probe. The inward formation can block back current that may be reflected from the antenna of the probe during operation.

In accordance with some embodiments, a microwave ablation probe is provided. The microwave ablation probe may include a cable extending in an axial direction and comprising an antenna configured to deliver Radio Frequency (RF) energy and an inner tube extending in the axial direction and positioned radially outward of the cable. The probe may also include an outer tube extending in the axial direction and positioned radially outward of the inner tube. The inner tube can include a crimped portion positioned a predetermined axial position along the inner tube.

In one aspect, the crimped portion can be integrally formed in the inner tube.

In another aspect, the crimped portion may include a first crimp being radially inwardly formed toward the cable.

In another aspect, the crimped portion may include a second crimp radially inwardly formed toward the cable.

In another aspect, the first crimp and the second crimp can be positioned at different planes oriented substantially perpendicular to the axial direction.

In another aspect, the first crimp and the second crimp can be positioned in the same plane oriented substantially perpendicular to the axial direction.

In another aspect, the first crimp and the second crimp can be oriented at offset circumferential positions around the axial direction.

In another aspect, an inner surface of the inner tube and the outer surface of the cable can define a first channel and the inner surface of the outer tube and the outer surface of the inner tube can define a second channel, and the first channel and the second channel define a flow path for cooling fluid to circulate in the microwave ablation probe.

In another aspect, the crimped portion may include a radially inwardly formed choke to reduce propagation of back current reflected from the antenna during operation.

In another aspect, a first channel defined between the cable and the inner tube and a second channel defined between the inner tube and the outer tube may form a cooling path for the circulation of cooling fluid through the probe.

In some embodiments of the present disclosure, a microwave ablation probe is provided. The probe may include a cable comprising an antenna configured to deliver Radio Frequency (RF) energy to a target zone and a cooling path defined by a first channel and a second channel configured to circulate cooling fluid in the probe. The inner tube may include a choke formed thereon configured to reduce RF energy reflected away from the antenna.

In one aspect, the choke may include a first crimp inwardly formed toward the cable.

In another aspect, the choke may include a second crimp inwardly formed toward the cable.

In another aspect, the first crimp and the second crimp may be formed at different axial locations on the inner tube.

In another aspect, the first crimp and the second crimp may be formed at offset circumferential locations.

In another aspect, the first crimp may be formed along a portion of the circumference of the inner tube.

In some embodiments of the present disclosure, a method of producing a microwave ablation probe is provided. The method may include positioning an inner tube over an outer surface of a cable comprising a microwave ablation antenna and radially crimping the inner tube at a choke distance. The choke distance can be at a predetermined axial distance away from microwave ablation antenna. The method may also include positioning an outer tube over the inner tube and the microwave ablation antenna.

In one aspect, the inner tube can be crimped to a crimp depth to position an inner surface of the inner tube at a predetermined location relative to an outer surface of the cable.

In another aspect, the inner tube can be crimped at a portion of a circumferential surface of the inner tube such that a distance between an inner surface of the inner tube and an outer surface of the cable is different at different circumferential locations around the cable.

In another aspect, the inner tube can be crimped at a first portion of a circumferential surface of the inner tube at a first axial position and at a second portion of the circumferential surface of the inner tube at a second axial position to result in two offset crimps.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The microwave ablation probes and antennas of the present disclosure can reduce the amount of current that is reflected along the feeding cable of the antenna to reduce the amount of undesirable heating that can be caused from such reflected current. The reflection of current along the antenna is undesirable because it can cause areas of body tissue to be heated and/or damaged that are not being targeted by the ablation treatment. The ablation probes and antennas of the present disclosure can produce a heating zone that is more spherical in shape than existing probes and antennas.

Microwave ablation probes are often used during ablation treatments to target undesirable tissues such as tumors. During such procedures, the ablation probe can be inserted into a body and be positioned at or near the target tissue. The microwave ablation antenna included in the probe can emit radio frequency (RF) energy such as microwave energy. The microwave energy can be fed to the antenna via a feeding cable that couples a microwave generator to the antenna. The microwave energy can travel from the microwave generator to the antenna in the form of current.

In many examples, the feeding cable is a coaxial cable that can include an inner conductor and an outer conductor. The current can travel from the microwave generator to the antenna on the surface of the cable inner conductor and the inner surface of the outer conductor. During a treatment procedure, the current on the inner conductor radiates into the target tissue heating the tissue. The current on the inner surface of the outer conduct can travel back (or can be reflected back) toward the microwave generator on the outer surface of the outer conductor of the feeding cable. This reflected back-current can radiate tissues that may be located adjacent to or near the feeding cable. This condition can be undesirable because the radiation of energy can heat and/or damage tissues other than the target tissue that is targeted for the treatment.

Existing probes and antennas attempt to mitigate the effects of this back-current or reflected current using various structures or methods. In some examples, additional structures are added to the microwave ablation probe to prevent or suppress the back-current or reflected current. These additional structures, however, add to the overall size or external profile (e.g., outer diameter) of the microwave ablation probe. An increase in size is undesirable because a larger size probe can be more damaging to healthy tissue that may be located proximate to the target tissue (e.g., the tumor).

Figure 1:
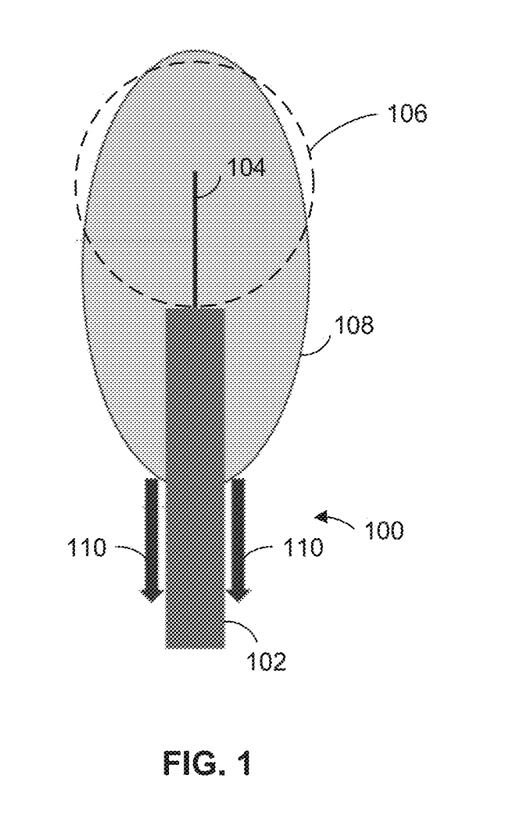
FIG. 1 is a side view illustration of an ablation antenna that produces an elongated heating zone.

Turning now to FIG. 1, an ablation antenna assembly 100 is shown. The ablation antenna assembly 100 can include a cable 102 and an antenna 104. The antenna 104 can extend outward from an end of the cable 102 to deliver RF energy such as microwave energy to a target zone 106. The target zone 106 can be a target tissue, for example, such as a tumor. During a treatment, the ablation antenna assembly 100 can be positioned in a probe assembly (not shown) and positioned at or near the target zone 106. The cable 102 can deliver energy to the antenna 104 to cause the antenna to emit RF energy, such as microwave energy, to the target zone.

During such a process, however, the current that travels from an energy source (e.g., a microwave generator) to the antenna 104 can be reflected and can travel back along the cable 102 in the form a back current 110. When the antenna 104 radiates the RF energy, the antenna heats the surrounding ablation zone 108 in the tissue of a body into which it is placed. If the antenna 104 were the only source of energy, the ablation zone 108 would be shaped in a circular shape or spherical shape centered around the antenna 104. But, since the back current 110 is traveling back along the cable 102 away from the antenna 104, the current heats the surrounding tissue. Because both the back current 110 and the antenna 104 are sources of heat energy, the abalation zone 108 that forms has an elongated shape that can be oval in the cross-section and have an ovoid shape in three dimensions. The elongated zone 108 can have an egg shape or capsule shape in some examples.

The elongated ablation zone 108 is undesirable in ablation treatment processes, because the elongated ablation zone 108 can heat, damage and/or destroy heathy or untargeted tissues. As shown the elongated ablation zone 108 is much larger and longer (in a direction along the axis of the cable 102) than the target zone 106. Such a condition can lead to undesirable outcomes when such ablation antenna assemblies (such as assembly 100) are used.

Figure 2:
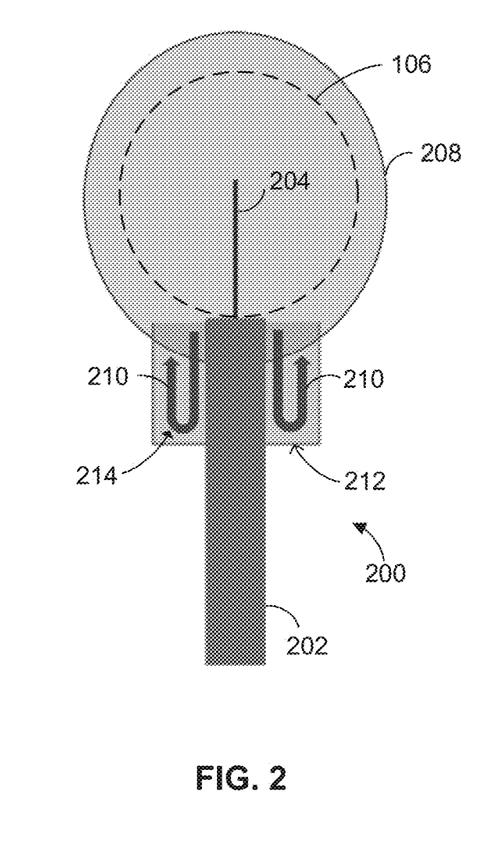
FIG. 2 is a side view illustration of an ablation antenna that produces generally spherical heating zone.

In some embodiments of the present disclosure, the problems of the ablation antenna assembly 100 are attempted to be mitigated by blocking or choking the back current and/or applying a cooling region to the ablation antenna as shown in FIG. 2. As shown, ablation antenna assembly 200 can include a cable 202, an antenna 204, a choke 212 and a cooling region 214. The cable 202 and the antenna 204 can operate as previously described with respect to assembly 100 to deliver RF energy to a target zone 106. The back current 210, however, is blocked by traveling along the cable 202 by the choke 212. The back current 210 is circulated at an end section of the cable 202. The cooling region 214 can be positioned at or near this same end region of the cable 202. The cooling region 214 can operate to actively cool the cable 202 so that the back current 210 does not heat tissue or other areas adjacent the cable.

Since the cooling region 214 prevents and/or reduces the amount of heating that may occur from the back current 210 and the back current 210 is limited from travelling beyond the end portion of the cable 202 by the choke 212, the ablation zone 208 can have a more circular or spherical shape as shown. As shown in FIG. 2, the ablation zone 208 is limited from extending or being elongated in a direction along an axis of the cable 202. The ablation zone 208 is shaped similarly to the target zone 106 and does not excessively extend beyond the target zone 106. In this manner, the ablation antenna assembly 200 can prevent and/or reduce the undesirable heating, damaging and/or destruction of tissues that are located outside of the target zone 106. Existing chokes can increase the size and/or outer diameter of the probe into which the antenna assembly 200 may be incorporated. It is desirable to maintain the size or outer diameter of the probe, however, so as to allow the probe to cause as little damage or disturbance to the body and tissue into which the probe may be inserted. In some examples, the outer diameter of the probe is about 2.1 mm or less. In other examples, the outer diameter of the probe has an outer size that is less than or equal to about a 14 gauge needle. In other examples, the probe can have other sizes. The methods and apparatuses of the present disclosure include chokes that do not require the size or the outer diameter of the probe to be increased.

Figure 3:
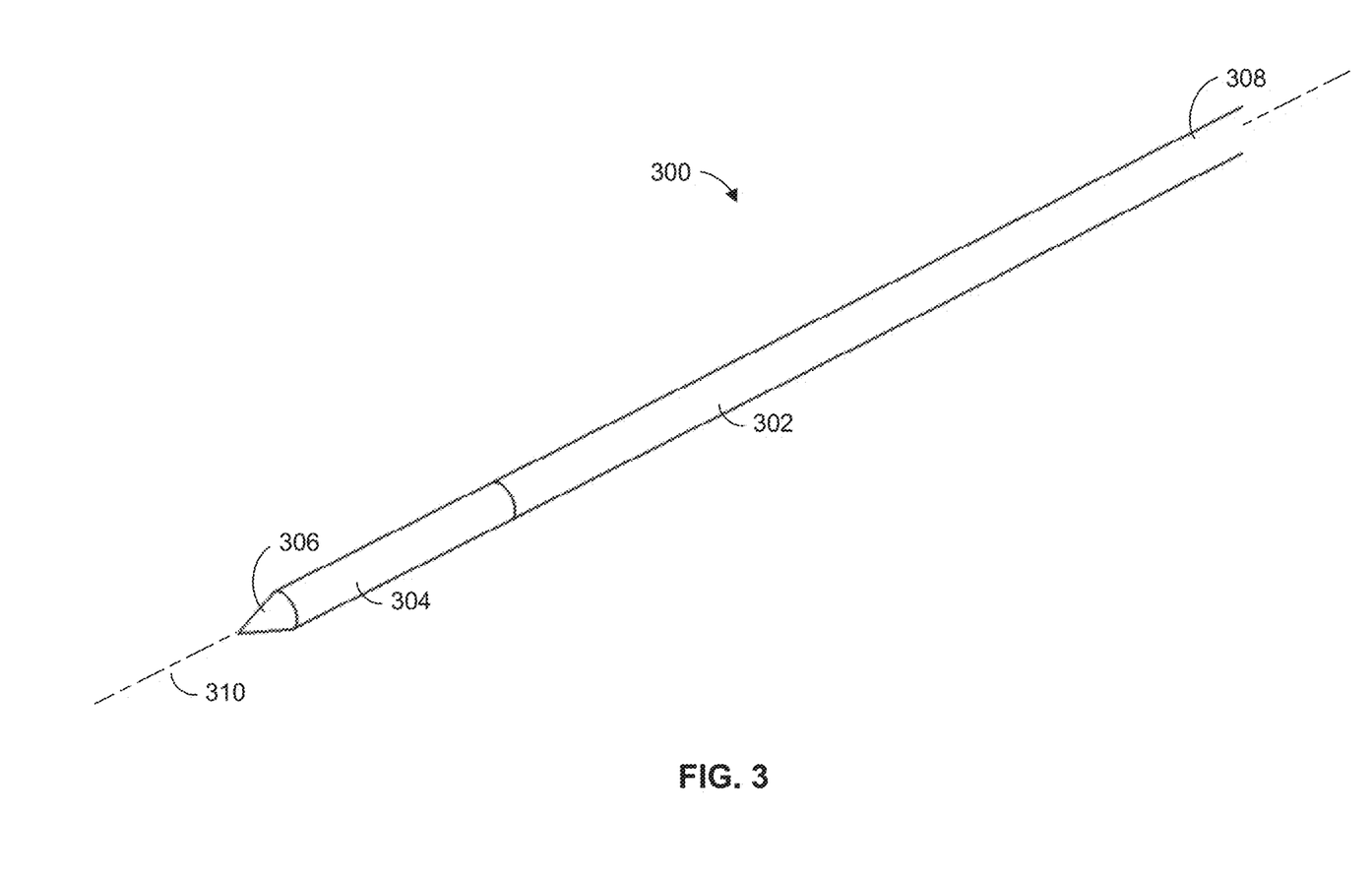
FIG. 3 is an isometric view illustrating an example ablation probe in accordance with the present disclosure.

Referring now to FIG. 3, an example ablation probe 300 is shown. The ablation probe 300 can include a shaft 302 and a tip section 304. The probe 300 can extend in an axial direction along axis 310. For purposes of the present disclosure, the terms axial and radial are used to generally describe directions relative to the axis 310. For example, an axial length, axial direction, or axial distance is a length, direction or distance that is oriented in a direction aligned and/or parallel to the axis 310. A radial length, a radial direction or a radial distance is a length, direction or distance that is oriented substantially perpendicular to the axis 310. As can be determined from the context, the radial length, direction or distance may originate or me measured from the axis 310 and outward therefrom.

The probe 300, as will be further described, can include an ablation antenna configured to heat tissue surrounding or positioned adjacent to the probe 300 in an ablation zone that surrounds a proximal end 306 of the probe 300. The ablation antenna can radiate RF energy, such as microwave energy, that is generated by a generator that travels from a distal end 308 of the probe toward the proximal end 306.

Figure 4:
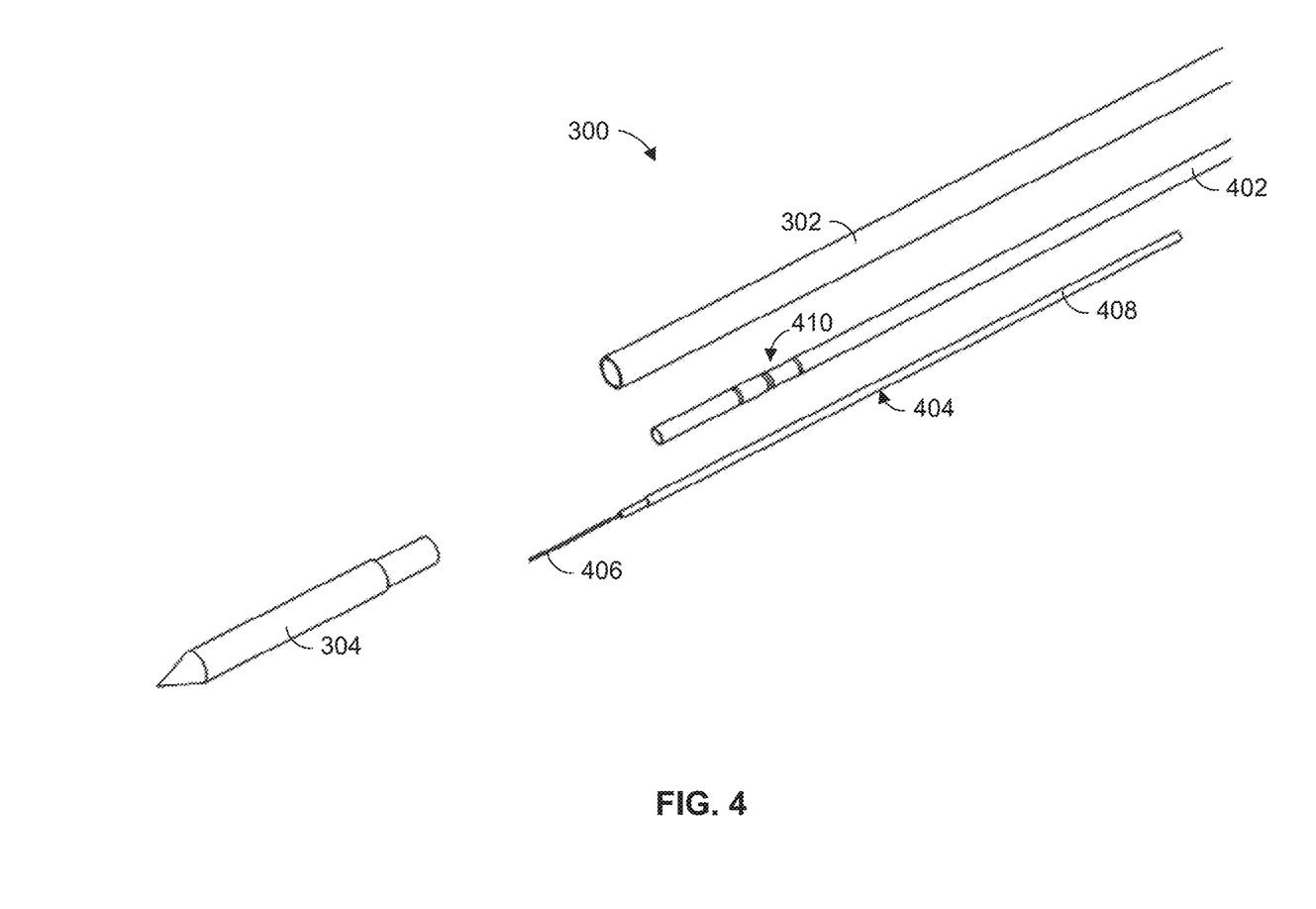
FIG. 4 is an exploded isometric view illustrating the example ablation probe of FIG. 3.
Figure 5:
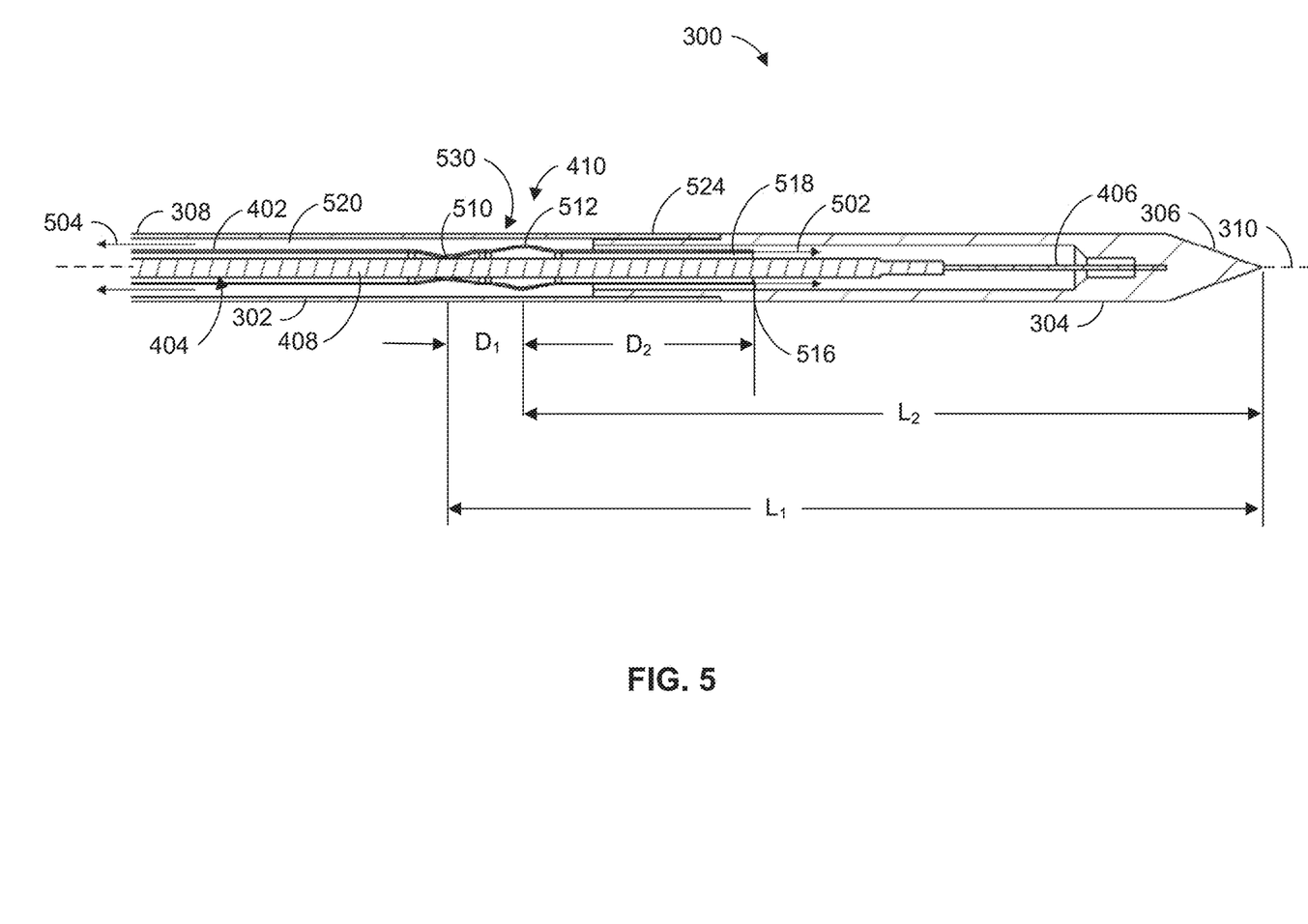
FIG. 5 is a cross-sectional side view illustrating the example ablation probe of FIG. 3.

Referring now to FIGS. 4 and 5, an exploded view and a sectional view of the probe 300 are shown. As can be seen, the probe 300 can include an inner tube 402, an ablation antenna assembly 404 that can be positioned inside the shaft 302 and the tip section 304 when the probe 300 is assembled. The antenna assembly 404 can be positioned inside the shaft 302 so that the antenna 406 is positioned adjacent or near the proximal end 306 of the probe. The cable 408 extends in an axial direction away from the antenna 406 toward the distal end 308. While not shown, the cable 408 can be coupled to a generator, such as a microwave generator, that can cause current to flow from the generator to the antenna 406 so that the antenna 406 radiates RF energy, such as microwave energy.

The cable 408 is substantially aligned along the axis 310 at the center of the probe 300. The inner tube 402 can be positioned concentrically along the axis 310 and radially outward of the cable 408. The inner tube can have an inner diameter that is greater than an outer diameter of the cable 408. In this manner, a circumferential channel 518 can be formed between the outer surface of the cable 408 and the inner surface of the inner tube 402. The inner tube 402 can extend into the shaft (or outer tube) 402 and terminate at terminating end 516.

The outer tube 302 can be substantially aligned along the axis 310 at the center of the probe 300. The outer tube 302 can be positioned concentrically along the axis 310 and radially outward of the inner tube 402 and the cable 408. The inner tube 402 can be positioned between the cable 408 and the outer tube 302. The outer tube 302 can have an inner diameter that is greater than the outer diameter of the inner tube 402. In this manner, a second circumferential channel 520 can be formed between the outer surface of the inner tube 402 and the inner surface of the outer tube 302. The tip section 304 can fit or be joined to the outer tube 302 at a probe joint 524. The tip section 304 can, for example, have a stepped portion that can fit inside the outer tube 302 at the probe joint 524. In other examples, the tip section 304 and the outer tube 302 can be joined at the probe joint 524 using other structures, fits such as a tapered section, an interference fit, a threaded portion or the like.

As further shown in FIG. 5, the probe 300 can operate to cool one or more portions of the probe 300. The first circumferential channel 518 and the second circumferential channel 520 can form a cooling flow path. A cooling fluid, such as water or other suitable fluid, can be caused to flow through the first circumferential channel 518 from the distal end 308 toward the proximal end 306 of the probe 300 as indicated by flow 502. The cooling fluid can then flow from the proximal end 306 toward the distal end 308 through the second circumferential channel 520 as indicated by flow 504. In this manner, the cooling fluid can be circulated though the probe 300. The cooling fluid can have a temperature that is lower than an ablation temperature of the probe 300. Thus, the cooling fluid that circulates through the probe 300 can operate to remove heat from one or more portions of the probe 300.

The probe 300 can also include a choke 530. The choke 530 can operate to block back current that otherwise would travel back along the cable 202 toward the distal end 308 of the probe 300. The choke 530, in this example, can be formed by crimping the inner tube 402. The inner tube 402 can be crimped at a first crimp 510 and a second crimp 512. The inner tube 402 can be crimped, for example, to reduce the gap between the outer surface of the cable 408 and the inner surface of the inner tube 402. In one example, the inner tube 402 is crimped at the first crimp 510 and/or the second crimp 512 such that a gap between the inner surface of the inner tube 402 and the outer surface of the cable 408 is less than or equal to about 1 mm. In other examples, the inner tube 402 can be crimped so as to touch and/or contact the cable 408. In still other examples, other gaps can be used.

As will be further explained below, the first crimp 510 and/or the second crimp 512 may be crimped such that the distance and/or gap between the inner tube 402 and the cable 408 is not substantially uniform around the circumference or periphery of the cable 408. In some examples, the first crimp 510 and/or the second crimp 512 is formed such that only a portion of the inner tube 402 around the circumference of the cable 408 is crimped toward the cable 408. The portion that is crimped toward the cable 408 can be different for each of the first crimp 510 and/or the second crimp 512. The first crimp 510 and/or the second crimp 512 can be formed using a suitable crimping tool or crimping die that can include a forming portion and/or a mandrel that can apply a force to the outer surface of the inner tube 402 during forming and can prevent deformation beyond a predetermined radial location, respectively.

In yet other examples, a forming tool can include one or more forming pins that are positioned at a desired location and can move inwardly toward the outer surface of the inner tube 402 to crimp the inner tube 402 at desired locations and to have a desired crimp size. In other examples, the first crimp 510 and/or the second crimp 512 can be formed using other methods and tools. In another example, the inner tube 402 can be formed in a single process step or in a multi-step process in which a length of tubing, such as stainless steel tubing, can be cut to a desired length and crimped as previously described. As can be appreciated, the cutting and crimping processes can be combined to increase process throughput and to reduce the cost of manufacturing.

As previously described, the first crimp and/or the second crimp can be integrally formed in the inner tube 402. When such crimps are integrally formed in the inner tube, the first crimp and/or the second crimp are formed without adding a separate component or part. The first crimp and/or the second crimp, when integrally formed, can be formed using a forming or crimping process that is applied to the inner tube 402. By integrally forming the choke by crimping the inner tube 402, the need for an additional part to make contact between the inner tube 402 and the cable 408 can be eliminated. Furthermore, the crimping process can preserve the integrity and flow path for the cooling fluid. No additional part or process is required to seal the flow path for the cooling fluid. Such advantages can make the probes of the present disclosure more cost effective, less complex and easier to manufacture than existing probes.

Figure 6:
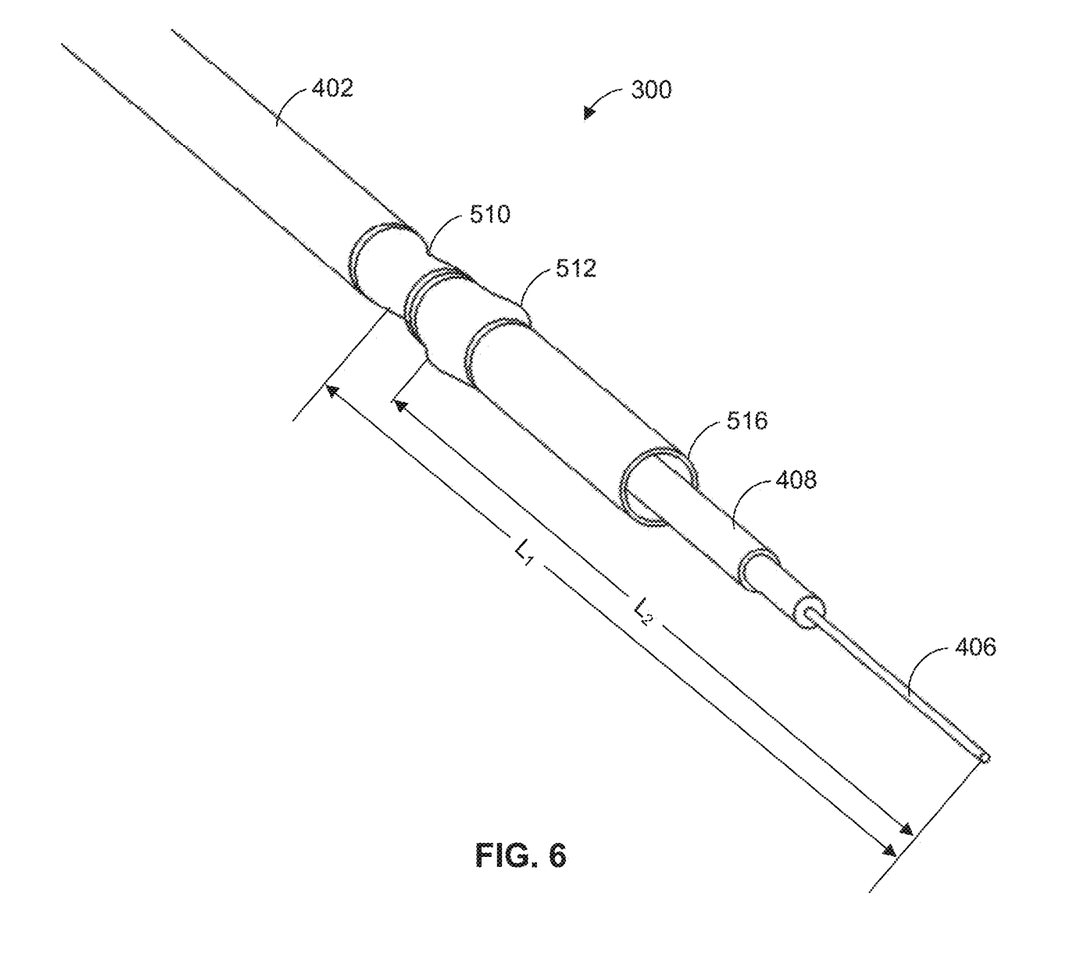
FIG. 6 is an isometric view of a proximal end of the example ablation probe of FIG. 3 with the outer tube and tip portion removed.

The first crimp 510 can be positioned at a predetermined axial crimp location along the probe 300. As shown, the first crimp 510 can be positioned at first axial crimp location L1 relative to a tip of the probe 300. The second crimp 512 can be positioned at a second axial crimp location L2 relative to a tip of the probe 300. The first crimp location L1 and/or the second crimp location L2 can also be positioned relative to a tip of the antenna 406 as shown in FIG. 6.

During operation of the probe 300 in an ablation procedure, a generator can send an RF signal in the form of current to the antenna 406 along the cable 408. The RF signal (such as a microwave) can radiate from the antenna 406 to heat and destroy a target tissue. The current can be reflected as a back current that can travel along the cable 408 toward the distal end 308. The choke 530 is positioned in the probe 300 to block the back current from travelling along the outer surface of the cable 408.

Also during operation, the cooling fluid can flow along the coolant path through the first circumferential channel 518 toward the antenna 406 and back away from the antenna in the second circumferential channel 520. Such a configuration can be operated and structured to cause an ablation zone to have a desired size and shape. The probe 300, for example, can be structured to cause a substantially spherical ablation zone to be produced during operation. In this manner, the ablation zone that is formed does not have an elongated shape or other shape that can heat or damage untargeted tissue.

Figure 7:
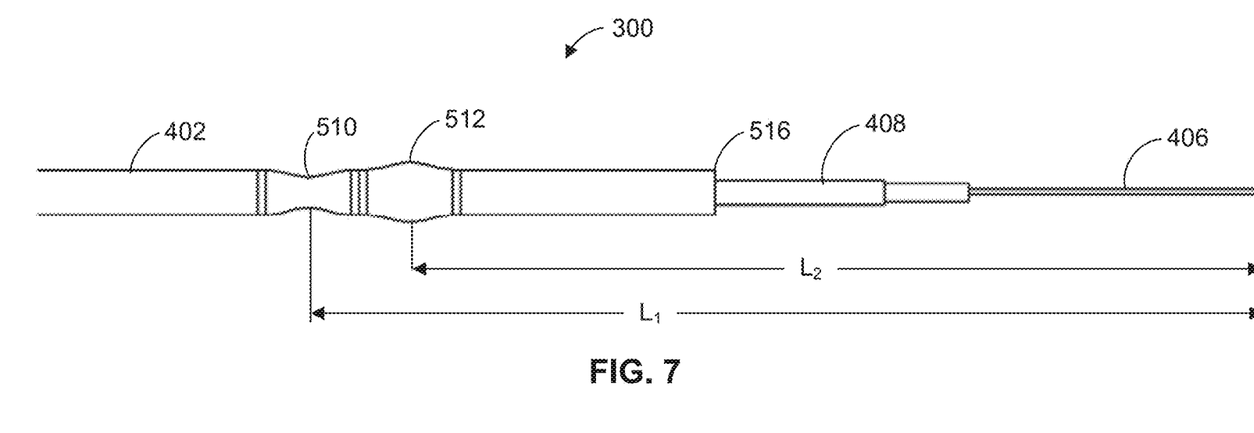
FIG. 7 is a front view of the example ablation probe shown in FIG. 6.
Figure 8:
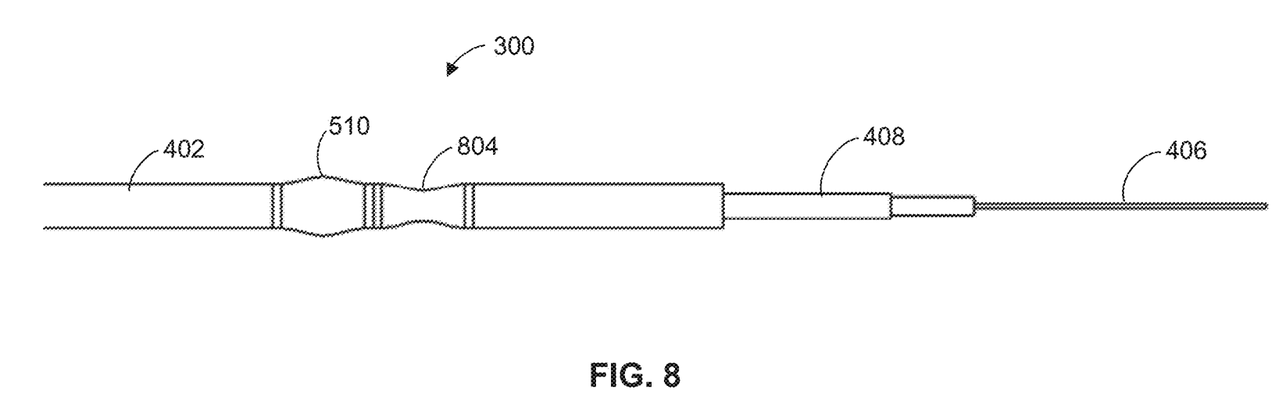
FIG. 8 is a plan view of the example ablation probe shown in FIG. 6.
Figure 9:
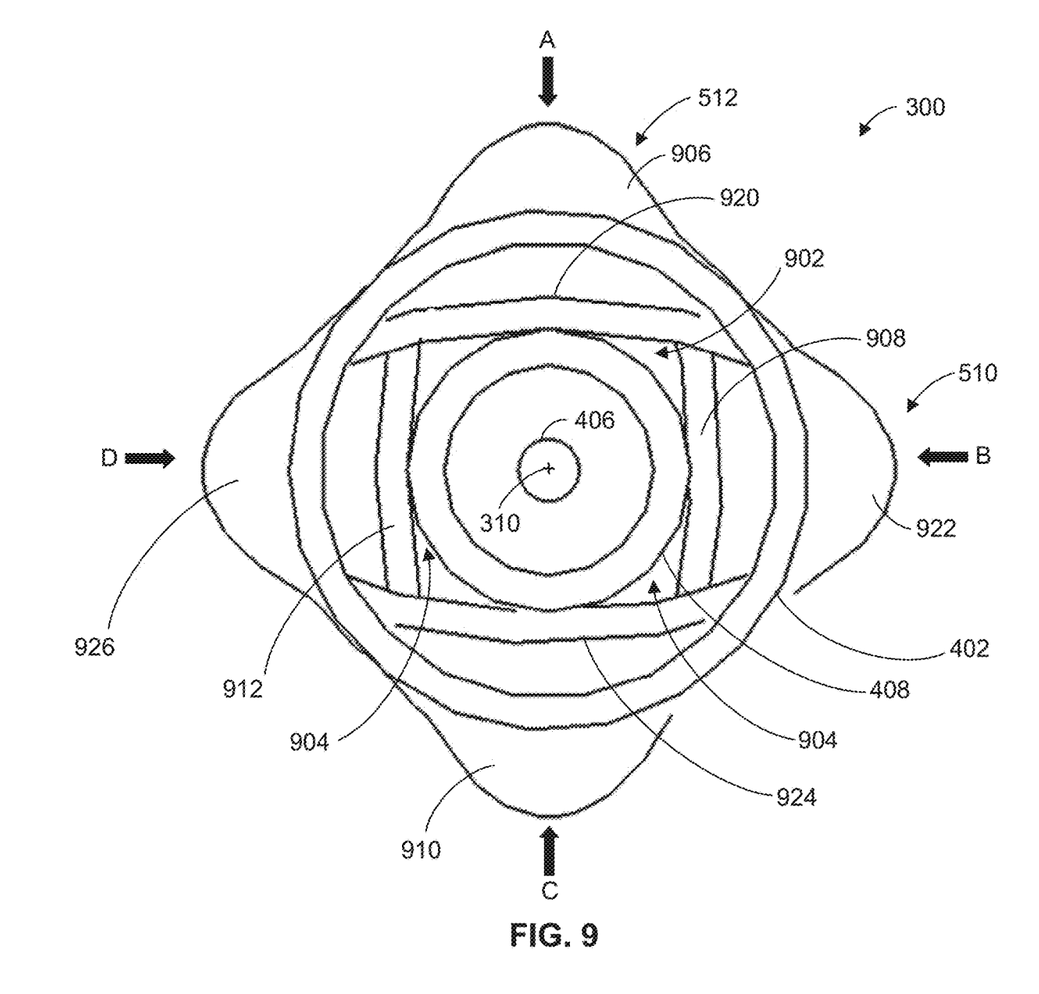
FIG. 9 is an end view of the example ablation probe shown in FIG. 6.

Turning now to FIGS. 7-9, example ablation probes are shown. For ease of illustration, the probes 300 and 800 shown in FIG. 7-9 are shown without the outer tube 302 or the tip section 304. With these elements removed, the crimp portions can be more easily shown. The probe 300 shown in FIG. 7 can have the structure as previously described. As shown, the probe 300, in this example, includes the first crimp 510 and the second crimp 512. The first crimp 510 and the second crimp 512 can be crimped to move a portion of the inner tube 402 toward the cable 408. In this example, the first crimp 510 and the second crimp 512 can be crimped at two circumferential locations approximately 90 degrees from each other. In example probe 300, the first crimp 510 can be crimped at a top and bottom of the inner tube in the orientation as shown. The second crimp 512, in this example, can be crimped at a front and back of the inner tube 402 in the orientation as shown. As can be appreciated, when the inner tube 402 is crimped a portion of the inner tube can be moved toward the cable 408. As this occurs, a different portion of the inner tube 402 can be deformed in a manner that moves the inner tube 402 away from the cable 408.

Referring now to FIG. 8, the probe 300 is shown in a plan view. As can be seen, the first crimp 510 has an outward deformation when viewed from the top. The second crimp 512 has an inward deformation when viewed from the top. As can be appreciated, the orientation of the first crimp 510 and the second crimp 512 can be reversed or oriented at different orientation with respect to the axis 310.

FIG. 9 shows an end view of the probe 300. As can be seen, the cable 408 and antenna 406 are positioned at the center of probe and are substantially centered about axis 310. The inner tube 402 can be positioned around the cable 408 and can be substantially centered around the axis 310. The first crimp 510 and the second crimp 512 are also shown from the end view. The first crimp 510 and the second crimp 512 can each include portions that are radially deformed inward toward the cable 408. The first crimp 510 and the second crimp 512 can also include portions that are radially deformed outward away from the cable 408.

The first crimp 510 can be formed at a circumferential position that is different from the circumferential location of the second crimp 512. In this manner, the portions that are deformed inwardly in the second crimp 512 are formed at different positions than the first crimp 510 to block more of the back current that travels along the cable 408. In the example shown, the first crimp 510 is positioned about 90 degrees circumferentially from the second crimp 512. In the example shown, the first crimp 510 can be formed by applying a force at locations indicated by arrows A and C. The force that is applied can deform the inner tube 402 inwardly toward the cable 408 to form a first inward portion 920 and a second inward portion 924. Such force that is applied can also cause the inner tube 402 to deform outwardly away from the cable 408. In this example, the formation of the first crimp 510 can also form the first outward portion 922 and the second outward portion 926. As shown, the first inward portion 920 and the second inward portion 924 can be positioned to have a gap 902 between the cable 408 and the first inward portion 920 and the second inward portion 924. The gap 902 can have any suitable size to block and/or reduce the amount of back current that will travel past the choke. In some examples, the gap 902 can be less than or equal to about 1 mm. In other examples, the gap 902 can be less than or equal to about 0.5 mm. In still other examples, the gap 902 can be about 0 mm.

The second crimp 512 can be formed, for example, by applying a force to the inner tube 402 at one or more circumferential locations. In this example, the second crimp 512 can be formed by applying a force at locations indicated by arrows B and D. The second crimp 512 can be formed similarly to first crimp 510 previously described but at the circumferentially offset position. The force that is applied can deform the inner tube 402 inwardly toward the cable 408 to form a third inward portion 908 and a fourth inward portion 912. Such force that is applied can also cause the inner tube 402 to deform outwardly away from the cable 408. In this example, the formation of the second crimp 512 can also form the third outward portion 906 and the fourth outward portion 910. As shown, the third inward portion 908 and the fourth inward portion 912 can be positioned to have a gap 904 between the cable 408 and the third inward portion 908 and/or the fourth inward portion 912. The gap 904 can have any suitable size to block and/or reduce the amount of back current that will travel past the choke. In some examples, the gap 904 can be less than or equal to about 1 mm. In other examples, the gap 904 can be less than or equal to about 0.5 mm. In still other examples, the gap 904 can be about 0 mm.

Since the first crimp 510 and the second crimp 512 are positioned at different circumferential locations, cooling fluid can flow between the cable 408 and the inner surface of the inner tube 402. In addition, the outward portions 906, 910, 922, 926 allow the flow of the cooling fluid even though flow may be restricted at the inward portions 908, 912, 920, 924. While not shown, the outward portions 906, 910, 922, 926 can be maintained to have an overall width or height to allow the inner tube 402 to be inserted into outer tube 302. As shown in FIG. 5, the outward portions can be controlled so that the second channel 520 is maintained and a gap exists between the outer surface of the outward portions and the inner surface of the outer tube 302. In this manner, the cooling fluid can flow over the outward portions between the inner tube 402 and the outer tube 302 in the flow path back toward the distal end 308.

With the offset of the first crimp 510 and the second crimp 512, the back current that may be reflected away from the antenna 406 can be blocked from travelling beyond the first crimp 510 and the second crimp 512 in an axial direction. In addition, the cooling fluid can flow along the flow path to cool the probe. The first crimp and the second crimp can be positioned at the first axial location L1 and at the second axial location L2 at predetermined locations to cause an abalation zone that is produced by the probe to have a desired shape such as a substantially spherical shape. In some examples, L1 and L2 can be positioned at locations in a range of about 2 mm to about 5 mm from the end of the probe. In another example, the first axial location L1 and the second axial Location L2 can be positioned in a range of about 3 mm to about 4 mm from the end of the probe.

In some examples, the first axial location L1 and the second axial location L2 can correspond to a first and a second crimp plane. For example, the first crimp 510 can be located in a first crimp plane and the second crimp 512 can be located in a second crimp plane. The first crimp plane and the second crimp plane can be oriented substantially perpendicular to the axis 310. In other examples, the first crimp plane and the second crimp plane can be oriented at other orientation relative to the axis 310.

In some examples, the first crimp plane and the second crimp plane can be located at distances D1 and D2, respectively, that are measured relative to the terminating end 516 of the inner tube 402. The distances D1 and D2 can be positioned based on the wavelength in medium of the electromagnetic signal at the operating frequency of the probe 300. The first crimp plane and the second crimp plane can be positioned at distance D1 and D2, respectively, that correspond to an odd multiple (i.e., 1, 3, 5 . . . ) of one-quarter of the wavelength in medium ($\lambda_m$) of the electromagnetic signal of the probe 300 at the operating frequency. For example, if the probe 300 is configured as a microwave ablation probe, the operating frequency of the probe can be about 2.45 GHz and a wavelength of the microwave can be approximately 122 mm. The cooling fluid of the probe 300 can, for example, be water. The wavelength in medium ($\lambda_m$) is equal to wavelength in free space divided by the square root of the permittivity of the medium in the cooling flow path. Thus, one-quarter of the wavelength in medium ($\lambda_m/4$) corresponds to about 3.46 mm for water. Thus, the distances D1 and D2 can correspond to odd multiples of 3.46 mm, in this example. In other examples, if other wavelengths, operating frequencies or mediums are used, the first crimp plane and the second crimp plane can be positioned at other distances.

In other examples, the probe can include more than two crimped locations or can include only one crimped location. In examples, with more than two crimped locations, the crimps may be offset at other circumferential positions such as at 30 degree intervals around the inner tube or at 45 degree intervals around the inner tube. The addition of more than two crimps can, for example, achieve improved mechanical stability and/or concentricity between the cable and the inner tube. In examples in which only one crimped location is used, the crimp can include inwardly formed portions located at more than two circumferential positions at a single axial location along the probe. In still other examples, other crimped formations can be used.

Figure 10:
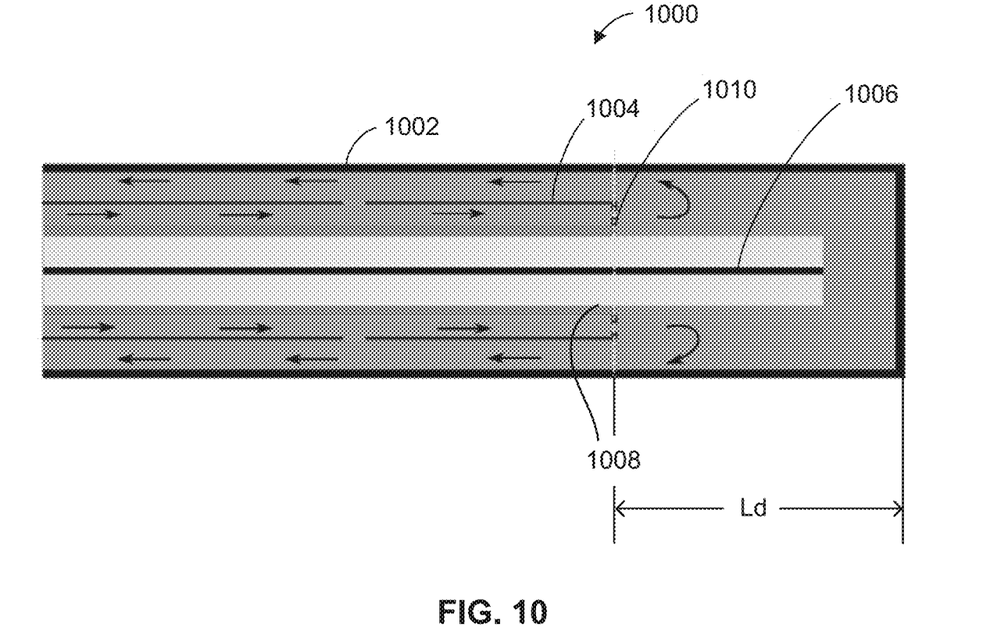
FIG. 10 is illustration of another example ablation probe in accordance with the present disclosure.
Figure 11:
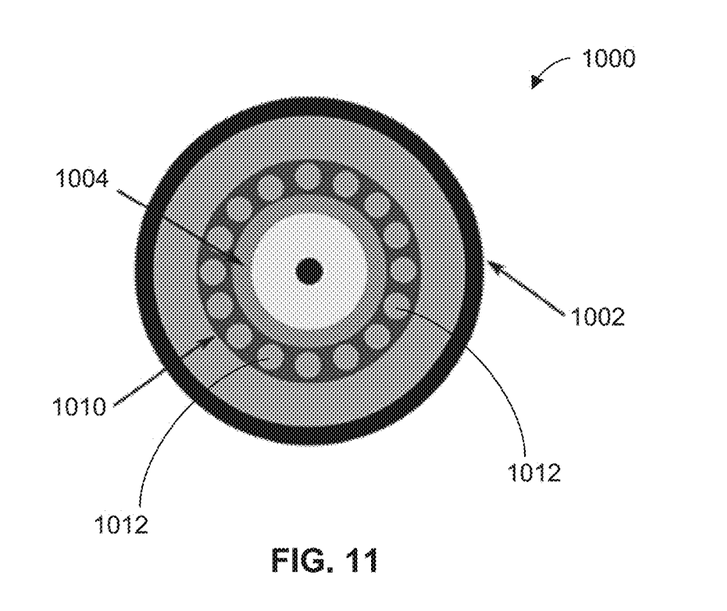
FIG. 11 is a cross sectional view of the example ablation probe of FIG. 10.

Referring now to FIG. 10, another example ablation probe 1000 is shown. In this example, the probe 1000 can include many of the structures previously described. The probe 1000 can, for example, include a choke that is formed as a disc 1010 positioned between the inner tube 1004 and the cable 1008. The disc 1010 can be positioned at a predetermined axial distance Ld away from the end of the probe 1000 and/or away from the end of the antenna 1006. As shown in FIG. 11, the disc 1010 can include one or more openings 1012. The openings 1012 can be sized such that the disc 1010 blocks the back current that may be reflected back along the cable 1008 away from the antenna 1006 but still allows sufficient cooling fluid to flow past the disc 1010 through the opening 1012. In other examples, the probe 1000 can include two or more discs 1010. In such multi-disc examples, the openings 1012 of adjacent discs 1010 can be circumferentially offset relative to one another to block back current but still provide a flow path for cooling fluid.

Figure 12:
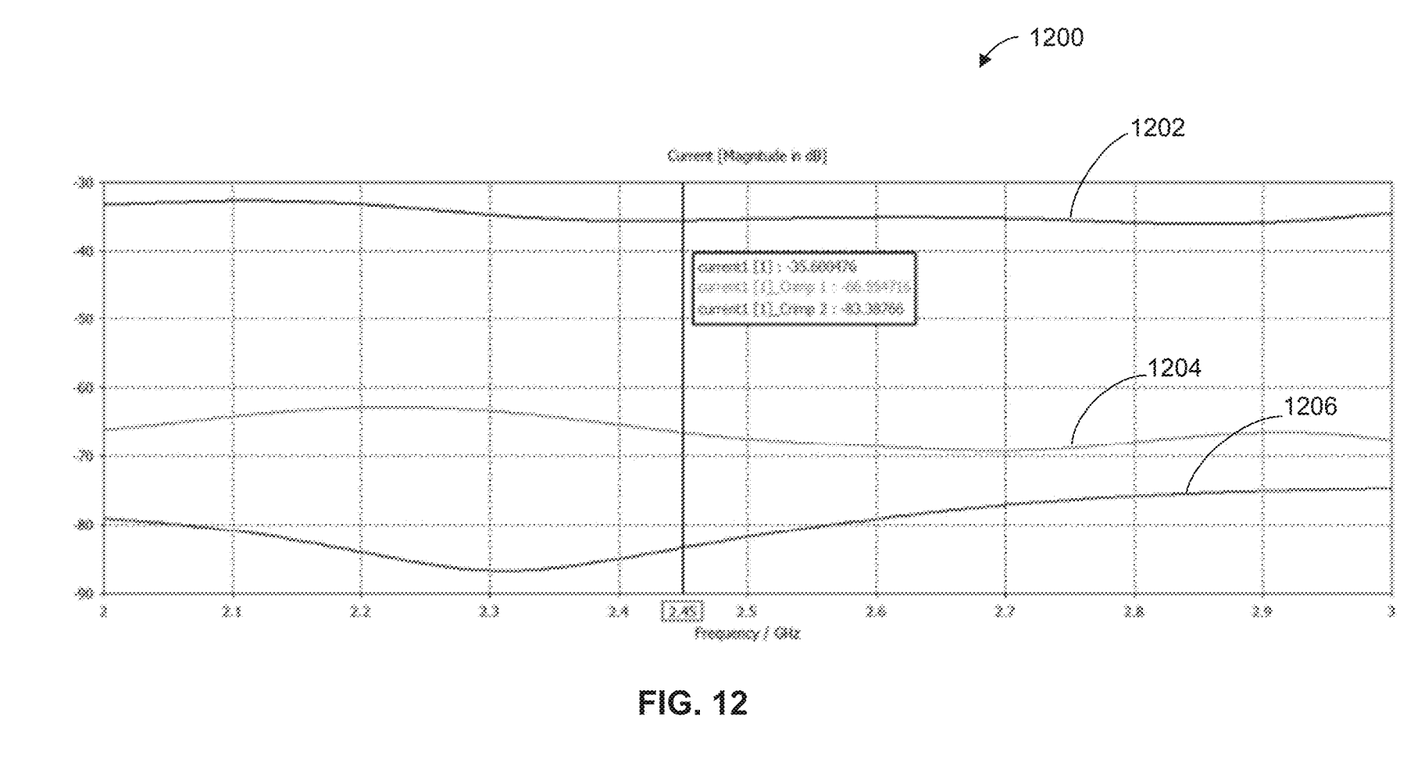
FIG. 12 is a graph showing a reduction in current caused by example chokes in the ablation probes of the present disclosure.

Experimental test results of the probes of the present disclosure confirm the improved performance of the probes over existing probes and existing ablation methods. In one example, a probe was tested that was structured similarly to the probe 800 previously described. The probe showed improved performance over a similar probe that do not include the crimped choke. As shown in FIG. 12, three probes were tested to measure the amplitude (in decibels, dB) of the back current on the probe. The line 1202 shows the performance of the probe that did include any choke (i.e., did not include the first crimp 510 or the second crimp 512). The line 1204 shows the performance of the probe that included only one crimped portion (i.e., first crimp 510). The line 1206 shows the performance of the probe that included two crimped portions (i.e., first crimp 510 and second crimp 512). As can be seen, the probe with one crimped portion performed better by blocking and thus having a lower amplitude of back current than the uncrimped probe of 1202. As further indicated by line 1206, the probe with two crimped portions, like the probe 800 previously described, performed the best of the three tested probes and thus had the lowest amplitude of back current. Further analysis of the test results described above demonstrated a 88% improvement of the one crimp sample versus no crimp and the two crimp example demonstrated a 137% improvement over the no crimp sample.

Figure 13:
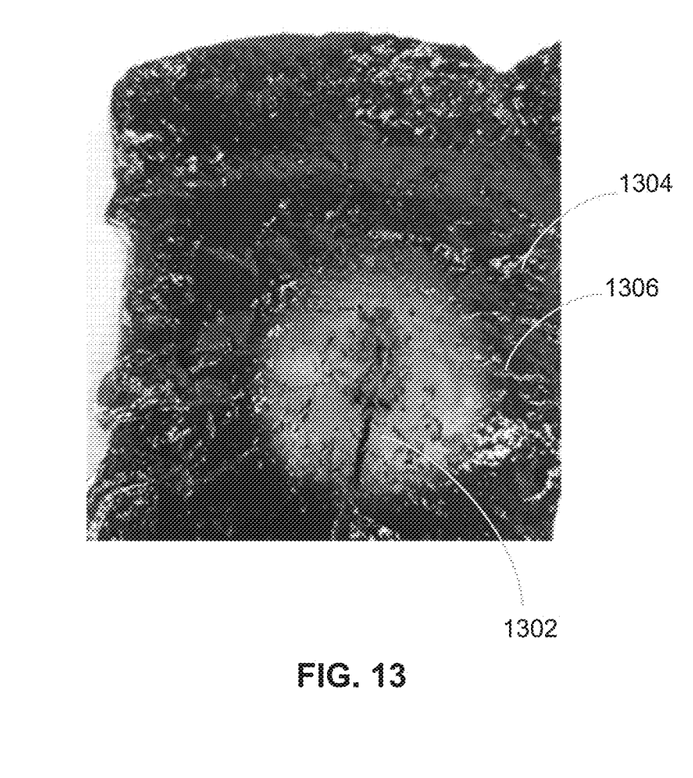
FIG. 13 is an image showing a heating zone in body tissue produced by an example ablation probe of the present disclosure.

The probes of the present disclosure were also tested in tissue samples to determine the ablation zones produced by the ablation probe. FIG. 13 shows one example ablation probe 1302 that was inserted into a bovine liver tissue sample 1304. The ablation probe 1302 was configured to include two crimped portions like the probe 800 previously described. The ablation probe 1302 was energized to produce an ablation zone 1306. In this test example, the ablation probe was energized at 78 watts for 10 minutes. As can be seen, the ablation zone 1306 produced by the has a substantially circular shape in which the height and width of the ablation zone 1306 are about the same in size. In this example, a width of the ablation zone 1306 measured about 40 mm and a height of the ablation zone 1306 measured about 42 mm. As such, the ablation zone 1306 was observed to have a substantially spherical shape.

As demonstrated by the experimental results, the probes of the present disclosure with the crimped choke portions demonstrate improved performance over existing probes. The probes of the present disclosure can produce symmetrical and/or spherical ablation zones in tissue such that they can be used to repeatedly and accurately target undesirable tissue for ablation treatment. Furthermore, the crimped portions in the probes of the present disclosure (or other choke structures as previously described) can be included in the probes without increasing the overall outer diameter of the probes.

In addition to the above, one or more methods of assembling and/or producing ablation probes is contemplated. In one example method, a microwave ablation prove can be produced by positioning an inner tube over an outer surface of a cable. The inner tube, the outer tube and the cable can be configured as previously described with respect to example probe 300. The cable can include an antenna for radiating microwave energy.

The method can also include radially crimping the inner tube at a distance away from the antenna. In some methods, the inner tube can be crimped prior to positioning the inner tube over the cable. In other methods, the inner tube can be positioned over the cable and then crimped. Any suitable crimping method can be used such as those previously described. In some examples, the inner tube can be crimped to a crimp depth to position an inner surface of the inner tube at a predetermined location relative to the surface of the cable. In some instances, the crimp depth provides for a gap. In other instances, the crimp depth provides for no gap between the inner tube and the cable at the crimp.

The crimp that is formed in the inner tube can be positioned at a portion of the circumferential surface of the inner tube. For example, the crimp can be formed at a selected circumferential portion and not at other circumferential portions. The crimp can be formed, for example, like the first crimp 510 and/or the second crimp 512 previously described. As stated above, the crimp can include an inwardly formed portion along a first portion of the circumferential surface at the crimp plane and an outwardly formed portion along a second portion of the circumferential surface at the crimp plane.

The method may also include forming a second crimp like the first crimp described above. The first and second crimps can be formed at different axial positions along the probe and at different circumferential positions so that the first crimp and the second crimp are axially and circumferentially offset.

The method can also include positioning an outer tube over the inner tube. The outer tube can be positioned concentrically with the inner tube and the cable as previously described with respect to probe 300.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A microwave ablation probe comprising:
a cable extending in an axial direction and comprising an antenna configured to deliver Radio Frequency (RF) energy;
an inner tube extending in the axial direction and positioned radially outward of the cable; and
an outer tube extending in the axial direction and positioned radially outward of the inner tube;
wherein the inner tube is crimped at a portion positioned at a predetermined axial position therealong to define a choke configured to reduce RF energy reflected away from the antenna.

2. The microwave ablation probe of claim 1, wherein a gap between an inner surface of the inner tube and an outer surface of the cable is less than or equal to about 1 mm.

3. The microwave ablation probe of claim 1, wherein the choke comprises a first crimp being radially inwardly formed toward the cable.

4. The microwave ablation probe of claim 3, wherein the choke comprises a second crimp radially inwardly formed toward the cable.

5. The microwave ablation probe of claim 4, wherein the first crimp and the second crimp are positioned at different planes oriented substantially perpendicular to the axial direction.

6. The microwave ablation probe of claim 4, wherein the first crimp and the second crimp are positioned in a same plane oriented substantially perpendicular to the axial direction.

7. The microwave ablation probe of claim 4, wherein the first crimp and the second crimp are oriented at offset circumferential positions around the axial direction.

8. The microwave ablation probe of claim 4, wherein the inner tube is crimped at the first crimp and/or the second crimp such that a gap between an inner surface of the inner tube and an outer surface of the cable is less than or equal to about 1 mm.

9. The microwave ablation probe of claim 8, wherein a first channel defined between the cable and the inner tube and a second channel defined between the inner tube and the outer tube form a cooling path for the circulation of cooling fluid through the probe.

10. The microwave ablation probe of claim 1, wherein an inner surface of the inner tube and an outer surface of the cable define a first channel and an inner surface of the outer tube and an outer surface of the inner tube define a second channel, and the first channel and the second channel define a flow path for cooling fluid to circulate in the microwave ablation probe.

11. The microwave ablation probe of claim 1, wherein the inner tube contacts the cable.

12. The microwave ablation probe of claim 1, wherein the inner tube is not substantially uniform around a circumference of the cable.

13. A microwave ablation probe comprising:
a cable comprising an antenna configured to deliver Radio Frequency (RF) energy to a target zone; and
a cooling path defined by a first channel and a second channel configured to circulate cooling fluid in the probe;
wherein an inner tube that defines a boundary between the first channel and the second channel is crimped to define a choke configured to reduce RF energy reflected away from the antenna.

14. The microwave ablation probe of claim 13, wherein the choke of the inner tube comprises a first crimp defined inwardly toward the cable.

15. The microwave ablation probe of claim 14, wherein the choke of the inner tube comprises a second crimp defined inwardly toward the cable.

16. The microwave ablation probe of claim 15, wherein the first crimp and the second crimp are at different axial locations on the inner tube.

17. The microwave ablation probe of claim 16, wherein the first crimp and the second crimp are at offset circumferential locations.

18. The microwave ablation probe of claim 14, wherein the first crimp is at a first portion of a circumference of the inner tube.

19. The microwave ablation probe of claim 13, wherein the inner tube contacts the cable.

20. The microwave ablation probe of claim 13, wherein the inner tube is not substantially uniform around a circumference of the cable.

* * * * *